United States Patent [19]

Ray et al.

[11] Patent Number: 5,501,981
[45] Date of Patent: Mar. 26, 1996

[54] METHOD AND APPARATUS FOR CHEMILUMINESCENT DETECTION OF SULFUR

[75] Inventors: John D. Ray; Neil Johansen, both of Boulder, Colo.

[73] Assignee: Sievers Instruments, Inc., Boulder, Colo.

[21] Appl. No.: 27,145

[22] Filed: Mar. 5, 1993

Related U.S. Application Data

[60] Continuation-in-part of Ser. No. 754,889, Sep. 6, 1991, Pat. No. 5,310,683, which is a division of Ser. No. 444,636, Dec. 1, 1989, abandoned, which is a continuation-in-part of Ser. No. 275,980, Nov. 25, 1988, abandoned.

[51] Int. Cl.[6] .................................................. G01N 21/76
[52] U.S. Cl. .......................... 436/123; 436/119; 436/122; 436/172
[58] Field of Search .................................. 436/102, 119, 436/122–123, 172; 422/52.91

[56] References Cited

U.S. PATENT DOCUMENTS 4,352,779  10/1982  Parks ............................ 422/52
4,678,756   7/1987  Parks ............................ 436/123
4,843,016   6/1989  Fine .............................. 436/106

Primary Examiner—Lyle A. Alexander
Attorney, Agent, or Firm—Beaton & Folsom

[57] ABSTRACT

An improved method and apparatus for the measurement of sulfur compounds is described. The system comprises a dual burner assembly for the conversion of sulfur-containing compounds to form sulfur monoxide and subsequent detection of sulfur monoxide by ozone-induced chemiluminescence. The dual burner assembly also provides for the conversion of hydrocarbons and other chemical constituents of the sample to simple molecules that do not interfere in the formation or detection of sulfur monoxide. The dual burner assembly eliminates the interference observed in the measurement of sulfur compounds from the sample matrix using flame-based or single burner devices for the production of sulfur monoxide and detection by ozone-induced chemiluminescence.

20 Claims, 3 Drawing Sheets

METHOD AND APPARATUS FOR CHEMILUMINESCENT DETECTION OF SULFUR

RELATED APPLICATIONS

The present application is a continuation-in-part of application Ser. No. 07/754,889 filed Sep. 6, 1991 for Process for Simultaneous Measurement of Sulfur and Non-Sulfur Containing Compounds now U.S. Pat. No. 5,310,683, which is a divisional application of application Ser. No. 07/444,636 filed Dec. 1, 1989 now abandoned, which is a continuation-in-part of application Ser. No. 07/275,980 filed Nov. 25, 1988 now abandoned.

FIELD OF THE INVENTION

The present invention relates to a process and apparatus for the chemiluminescent detection of sulfur and, in particular, to the chemiluminescent detection of sulfur using a first burner to oxidize hydrocarbon compounds in a sample and then a second burner to produce sulfur monoxide for reaction with ozone to generate chemiluminescent sulfur dioxide.

BACKGROUND OF THE INVENTION

The presence of low levels of sulfur compounds in hydrocarbon and other chemical streams causes serious problems in the refining of petroleum products, the production of plastics, and other chemical processes. Even at parts per billion concentrations, sulfur compounds can poison the expensive catalysts used in refining and chemical processing. As a result of these and other problems with sulfur contamination, a wide variety of analytical techniques have been developed to identify and quantify trace levels of sulfur-containing compounds in different sample matrices.

Current and pending regulations limit the total sulfur content in fuels and other hydrocarbon products. For example, proposed new standards for gasoline and diesel fuels are 40 mg S/kg and 500 mg S/kg respectively. The desired specifications for total sulfur content of polymer grade ethylene and propylene are 50 ppb (0.05 mg S/kg). These new specifications will require improved methods for the determination of total sulfur content in these hydrocarbons which provide higher sensitivity and selectivity than existing methods.

Techniques for the measurement of total sulfur content include x-ray fluorescence, conversion of sulfur compounds to hydrogen sulfide followed by radiometric colorimetry detection, and combustion of sulfur compounds to form sulfur dioxide with detection by UV fluorescence and other techniques. The detection limits for these techniques are typically in the high parts per million range and cannot be used for the measurement of sulfur at low parts per million or parts per billion concentrations.

In some cases, it is desired to measure the concentrations of individual sulfur-containing compounds. This requires the use of a chromatographic technique to separate the sulfur species for subsequent detection, usually using a sulfur-selective detector. In other cases, only the total concentration of sulfur species is required, which eliminates the need for chromatographic separation.

Representative of the prior art for sulfur-selective chromatographic detectors is the flame photometric detector (FPD) described in U.S. Pat. No. 3,489,489 by Brody and Chaney for Flame Photometric Detector with Improved Specificity to Sulfur and Phosphorus. Sulfur compounds are combusted in a hydrogen-rich/air flame to produce electronically excited diatomic sulfur ($S_2^*$). The emission of radiation from this species is monitored using a photomultiplier tube (PMT) and an optical filter. Since the emitting species is short-lived, the PMT and filter are positioned in close proximity to the flame. The FPD has a non-linear and compound-dependent response for sulfur compounds. The response of the detector is dramatically decreased or quenched when sulfur compounds coelute from the chromatographic system at the same time as larger amounts of non-sulfur species, particularly hydrocarbons.

An improved FPD was described by Patterson and employs a dual flame design. The first hydrogen/air flame is used to partially combust the sample and minimize perturbation in the temperature of the second hydrogen/air flame, where the emitting species is formed upon additional reactions. This design served to reduce the quenching of the sulfur response due to coelution of hydrocarbons, however, quenching is not completely eliminated and this FPD design also has a compound-dependent, non-linear response for sulfur compounds.

Despite these limitation of the FPD, several systems for the measurement of total sulfur content have been developed using the FPD. A method and apparatus for the determination of carbon and sulfur content of hydrocarbon samples was described by Szakasits and Krc using a combination of gas chromatography, and oxidizing furnace to convert hydrocarbon to $CO_2$ and sulfur compounds to $SO_2$ and subsequent detection of $CO_2$ by infrared absorption and detection of $SO_2$ using an FPD. A total sulfur analyzer based on gas chromatographic separation of sulfur compounds, catalytic hydrogenation of sulfur compounds in a ceramic pipe reactor to form $H_2S$ and detection of $H_2S$ using an FPD is described in U.S. Pat. No. 5,049,508 by Hilscher, et al. for Apparatus and Process for Total Sulfur Determination. Hydrocarbons in the sample are hydrogenated to produce low molecular weight compounds. The pipe reactor is constructed from high purity alumina (>99.8% pure) and operated at elevated temperatures, preferably 1150° C.±2° C. The detection limit of this analyzer is reported to be 0.3 mg S/kg.

In both of these total sulfur analyzer, an FPD is used for the detection of the sulfur species and therefore these analyzers suffer from the limitation of the FPD. Specifically, there is a non-linear response and potential quenching of the sulfur response due to the presence of non-sulfur species.

A sulfur detection system that employs ozone-induces chemiluminescence has been described in U.S. Pat. Nos. 4,352,779 and 4,678,756, both by Parks. The sample is first passed through a furnace containing a heated metal oxide catalyst to oxidize the sulfur compounds and the other species in the sample matrix. The resultant gas stream is then dried and enters a second furnace where the stream is mixed with hydrogen to reduce the sulfur compounds to form hydrogen sulfide. The gas stream is then dried a second time and enters a chemiluminescent reaction chamber where it is mixed with ozone. Hydrogen sulfide will undergo a multi-step reaction with ozone to produce sulfur dioxide in an electrically excited state which emits light in the blue and ultraviolet region of the spectrum:

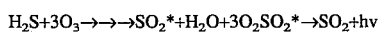

$$H_2S+3O_3 \rightarrow \rightarrow \rightarrow SO_2^*+H_2O+3O_2 \quad SO_2^* \rightarrow SO_2+h\nu$$

The major advantage of the chemiluminescent detection system of Parks over previous FPD-based systems is that a linear response for sulfur compounds is obtained. However, there are serious limitations to the detection scheme disclosed by Parks. To overcome interference from the sample matrix, a furnace containing a metal oxide catalyst, such as granular copper/copper oxide is employed. As described by Parks, the catalyst must be regenerated, either by stopping the analyzer and passing oxygen gas over the catalyst bed, or continuously feeding oxygen to the catalyst bed. This is because, as previously noted, sulfur compounds are known to poison catalysts, by reducing their effectiveness and eventually requiring replacement or regeneration of the catalysts.

Another disadvantage of the Parks process is the requirement for drying the gas stream, not once, but twice. Drying is required after the oxidation catalyst bed, presumably to improve the reaction efficiency of the hydrogenation reaction. Drying is also required after the hydrogenation reaction. Hydrogen sulfide, the product of the hydrogenation reaction will react with water yielding products that will not chemiluminescence with ozone, thus requiring the second drying procedure.

Another serious limitation of the Parks process and also of the Hilscher, et al. process, is the reactivity of $H_2S$. Adsorption and loss of hydrogen sulfide on tubing and other components of the analyzers is well known, particularly at low parts per billion levels. This limits the sensitivity of these analyzers to the high parts per billion or even parts per million levels of sulfur.

Finally, the chemiluminescent reaction of $H_2S$ with $O_3$ described in the Parks' patents is a multi-step reaction. Since the emitting species is $SO_2^*$, a large excess of $O_3$ is required to ensure formation of the emitting species and operating conditions of the analyzer must be adjusted to permit the reactions to occur in front of the photomultiplier tube.

An improved sulfur chemiluminescence detection system was adapted for chromatography detection in U.S. application Ser. Nos. 07/759,105 for Apparatus for Simultaneous Measurement of Sulfur and Non-Sulfur Containing Compounds and 07/754,889 for Process for Simultaneous Measurement of Sulfur and Non-Sulfur Containing Compounds, both by Godec, et al., and assigned to the assignee of the present invention. In the SULFUR CHEMILUMINESCENCE DETECTOR (SCD) brand detector disclosed therein, sulfur monoxide is produced from the combustion of sulfur containing compounds in a hydrogen-rich/air flame. The flame gases are then collected and transferred to a reaction with ozone in a single step to produce electronically excited sulfur dioxide, which emits light in the blue and ultraviolet regions of the spectrum:

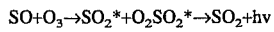

$$SO+O_3 \rightarrow SO_2^* + O_2 SO_2^* \rightarrow SO_2 + h\nu$$

This process has been used for atmospheric monitoring, and has also been combined with a conventional flame ionization detector to provide simultaneous detection of hydrocarbon and sulfur compounds in chromatographic analyses.

An improved burner for the production of sulfur monoxide and subsequent detection of sulfur monoxide by ozone-induced chemiluminescence has been recently described in application Ser. No. 07/824,852 filed Jan. 23, 1992 for Method and Apparatus for the Measurement of Sulfur Compounds by Shearer and assigned to the assignee of the present invention. A ceramic burner is used in place of the hydrogen/air flame to provide increased sensitivity and ease of operation for the measurement of sulfur-containing compounds in chromatographic analyses.

Common to these sulfur chemiluminescent detection systems are several important advantages over existing methods. The response of these systems for sulfur compounds is linear over at least four orders of magnitude. The response is not compound-dependent, but rather an equimolar response is obtained for all sulfur compounds, and there is no quenching of the sulfur response due to co-elution of hydrocarbons, provided the levels of hydrocarbons do not exceed several milligram of carbon per second. No intermediate oxidation, hydrogenation or drying steps are required. Sulfur monoxide is also less reactive than hydrogen sulfide and low parts per billion levels of sulfur compounds can be easily measured, indicating that adsorption and loss of SO is not as much of a problem as with $H_2S$.

The major disadvantages of these sulfur chemiluminescent detection systems is the selectivity versus hydrocarbons. While selectivites of $>10^6$ S/C are obtained when the SCD is used in conjunction with chromatography, higher selectivites are required for non-chromatography analyses and continuous, on-line monitoring. In the previous SCD's when a large sample of hydrocarbon is analyzed, the hydrocarbon is not completely combusted in the flame or ceramic burner resulting in a detector response due to chemiluminescent reactions of ozone with the unburned or partially burned hydrocarbon. Using a chromatographic column to produce a broad hydrocarbon peak decreases but does not eliminate this interference by reducing the amount of hydrocarbon reaching the flame or burner at any given time; however, the use of a chromatographic column is not desired for use in a total sulfur analyzer.

Other art in the field includes U.S. Pat. Nos. 4,843,016 by Fine; 4,717,675 by Sievers, et al; 4,077,774 by Neti; 4,097,230 by Patterson; 3,880,587 by Szakasits; and ASTM Standard D2622, *Annual Book of ASTM Standards*, Vol. 05.02, ASTM Philadelphia, Pa. 1990; ASTM Standard D1552, *Annual Book of ASTM Standards*, Vol. 05.01, ASTM Philadelphia, Pa.

SUMMARY OF THE INVENTION

The present invention is an improvement over the prior art and is specifically directed at eliminating hydrocarbon interference to allow applications of the detection scheme in total sulfur determinations. In the present invention a double burner configuration is employed prior to the chemiluminescent detector. Sulfur-containing compounds in either a gaseous, liquid or solid sample are introduced into the system, mixed with a controlled amount of oxygen, air or other chemical oxidizing agents and transferred to a heated ceramic or quartz combustion assembly. This first combustion assembly is operated under oxidizing conditions to convert hydrocarbons and other components of the sample matrix to $CO_2$, $H_2O$ and other simple compounds that do not undergo chemiluminescent reactions with ozone. Sulfur compounds in the sample are also converted in the first burner, presumably to oxides of sulfur, however the exact products formed in the reactions of sulfur compounds in the first burner are not important. A portion of the effluent of the first burner is then directed through a restrictor to the inlet of a second burner where it is mixed with a controlled amount of an oxidant such as oxygen or air and enters a second heated ceramic or quartz combustion zone. A controlled gas flow of a fuel such as hydrogen is also introduced to the heated combustion zone and mixes with the sample stream and oxidant stream. In the second combustion zone, sulfur compounds are converted to sulfur monoxide and other products.

The gaseous products from the second combustion zone are collected by means of a vacuum pump and are transferred to a chemiluminescent reaction chamber. In the chemiluminescent reaction chamber, the gaseous products are mixed with ozone. Sulfur monoxide reacts with ozone to produce electronically excited sulfur dioxide ($SO_2^*$) which relaxes by emission of light in the blue and ultra-violet region of the spectrum. The emitted light is monitored using a photomultiplier tube or similar light detection element. An optical filter can be used to limit the wavelengths of radiation reaching the light detection element. The electronic signal from the light detection element is electronically processed and amplified to produce an analog or digital signal that is proportional to the amount of radiation emitted in the chemiluminescent reaction chamber, which is in turn proportional to the amount of sulfur-containing compounds present in the sample. The analog or digital signal is then further processed using an electronic integrator, recorder or computer. Calibration of the system is performed by analyzing a sample with a known concentration of sulfur compounds.

The present invention is most suitable for the measurement of total sulfur content of samples without prior separation of the individual components by chromatography. However, the detection system can also be used with gas, liquid, supercritical fluid or other forms of chromatography to first separate the individual sulfur-containing components in a sample prior to detection with the double burner/chemiluminescence system.

The key element of the present invention is the use of an initial combustion assembly for the oxidation of the major components in the sample, without the use of a catalyst. The design of the first combustion assembly and the operating conditions of this assembly provide for complete or nearly complete oxidation of the sample matrix. The use of a restrictor to sample a portion of the effluent from the first combustion assembly into the second combustion assembly permits gas flow rates, reaction time and other operational parameters of the first combustion assembly to be optimized independent of the reaction conditions and gas flow rates employed in the second combustion assembly or chemiluminescence detector. The use of this first combustion assembly overcomes the interference from hydrocarbons or other chemical compounds that is observed in the prior art.

Another important element of the present invention is that it is not necessary to dry the effluent stream from either combustion assemblies. Parks employs a metal oxide catalyst bed for the oxidation of the sample but must dry the catalyst effluent prior to hydrogenation and must also dry the hydrogenated stream prior to chemiluminescence, presumably due to reactions of hydrogen sulfide with water to form species that will not chemiluminescence with ozone. In the present invention water produced in the oxidation of the sample matrix in the first combustion assembly does not affect the formation of sulfur monoxide in the second combustion assembly and therefore it is not necessary to dry this stream. Since sulfur monoxide will not react with water, it is also not necessary to dry the stream prior to chemiluminescent detection, thus greatly simplifying and improving the method of Parks.

DESCRIPTION OF THE PREFERRED EMBODIMENT

Figure 1:
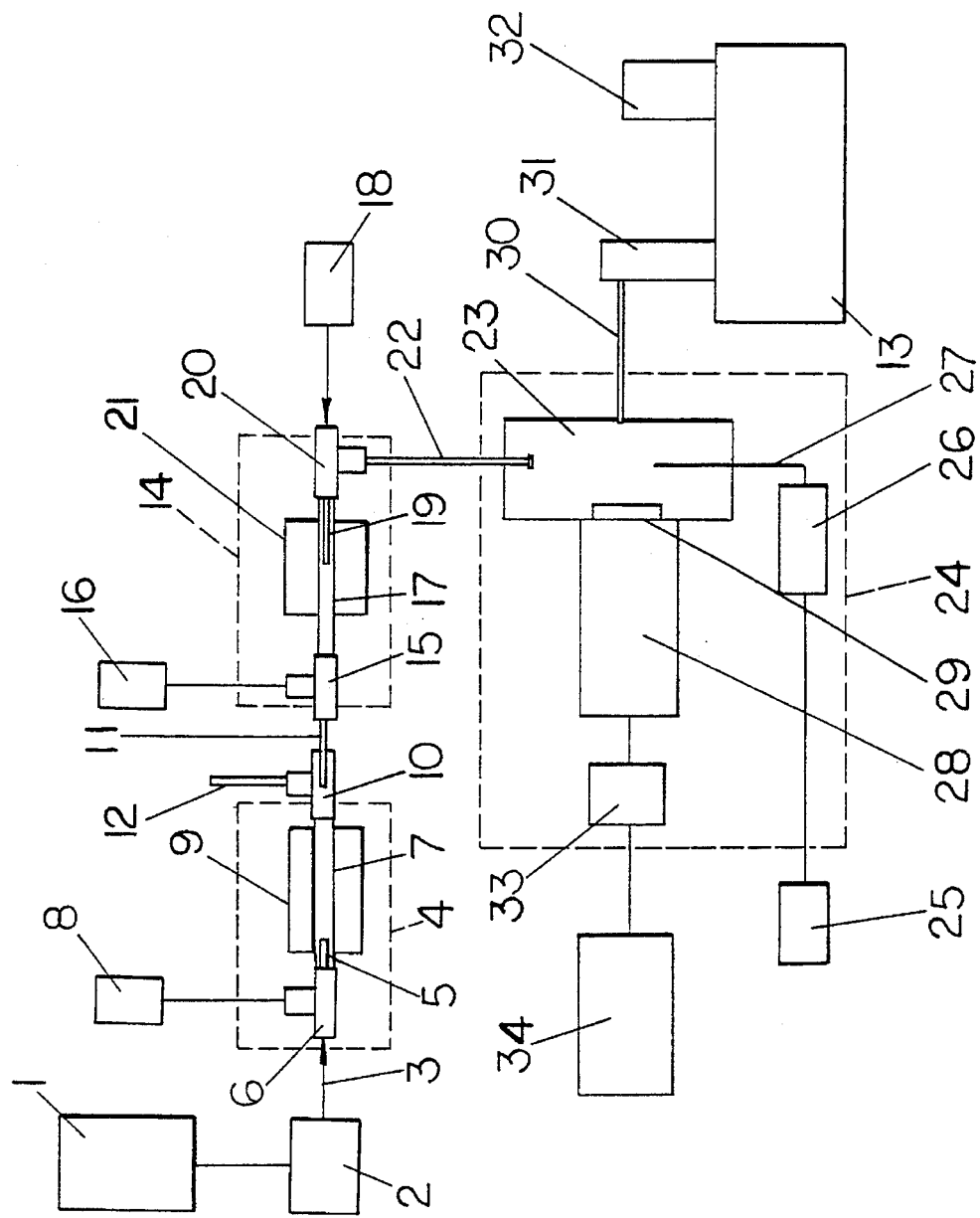
FIG. 1 is a schematic diagram of the invention.

FIG. 1 shows a generalized schematic of the total sulfur analyzer with a double burner assembly for the oxidation of the major components of the sample matrix prior to conversion of the sulfur-containing compounds in the sample to sulfur monoxide and subsequent detection of the sulfur monoxide by ozone-induced chemiluminescence. The carrier fluid 1 and sample inlet system 2 are representative of the various techniques that can be used to introduce the sample into the total sulfur analyzer. For example, in one embodiment, the carrier fluid 1 is a carrier gas and the sample inlet system 2 is a multi-port gas sampling valve for the injection of known volumes of gaseous samples into the analyzer. In another embodiment, the carrier fluid 1 is a carrier gas and the sample inlet system 2 is a multi-port liquid sampling valve for the injection of known volumes of liquid samples into the analyzer. In another embodiment, the carrier fluid 1 is a carrier gas and the sample inlet system 2 is a heated injection port for the injection of known volumes of gases or liquid samples into the analyzer using a syringe. In another embodiment, the carrier fluid 1 is a carrier gas and the sample inlet system 2 is a high temperature pyrolysis injector for the pyrolysis of solid samples and injection of the volatilized components into the analyzer.

In an alternative embodiment, the total sulfur analyzer with a double burner assembly can be used as a detector after chromatographic separation of the sample. In this embodiment, the carrier fluid 1 is a carrier gas, supercritical fluid, or suitable liquid mobile phase, and the sample inlet system 2 is a gas chromatograph, supercritical fluid chromatograph or liquid chromatograph.

For all of the above embodiments, the effluent 3 of the sample inlet system 2 is a gaseous stream containing sulfur compounds and other constituents of the sample, which is introduced into the first burner assembly 4 by means of a restrictor tube 5. The restrictor tube 5 extends through a mixing tee 6 and into a combustion tube 7 in the first burner assembly 4. An oxidant, such as air or oxygen is delivered from the oxidant supply 8, mixed with the sample stream via mixing tee 6 and enters the combustion tube 7. The combustion temperature of the combustion tube typically operates in a range from 400° to 1200° C. The combustion tube 7 may be packed with glass wool or another non-catalytic material to facilitate mixing of the oxidant and sample stream and to provide an inert surface for the oxidation of the constituents of the sample stream to produce carbon dioxide, water and other products. The flow rate of oxidant from oxidant supply 8 is controlled so as to provide an stoichiometric excess of oxidant to ensure complete oxidation of the sample stream.

The outlet of the combustion tube 7 is connected to an outlet tee 10 which in turn is connected to a second burner assembly inlet restrictor 11 and an outlet vent 12. A portion of the gaseous products from the first burner assembly 4 are collected by means of a vacuum pump 13 and the second burner assembly inlet restrictor 11 and are transferred to the second burner assembly 14. The remainder of the gaseous products from the first burner assembly 4 are exhausted out an outlet vent 12. In one embodiment, the second burner assembly inlet restrictor 11 is a metal, plastic, ceramic or quartz tube having a small inside diameter. The amount of gaseous products transferred to the second burner assembly 14 can be varied by using different lengths and different diameters of tubing for the second burner assembly inlet restrictor 11.

The outlet of the second burner assembly inlet restrictor 11 is connected to a second burner assembly inlet tee 15. An oxidant supply 16 is also connected to the second burner assembly inlet tee 15. The gaseous products collected from the first burner assembly 14, via the second burner assembly inlet restrictor 11 are mixed with oxidant from oxidant supply 16 in the second burner assembly inlet tee 15 and enters a ceramic tube 17 in the second burner assembly 14. A fuel supply 18 is connected to a fuel delivery tube 19 which is connected to a second burner assembly outlet tee 20. The fuel delivery tube 19 is positioned to deliver fuel near the center of ceramic tube 17 where the fuel mixes with the oxidant from oxidant supply 16 and the gaseous products collected from the first burner assembly 14 to produce a combustion reaction inside ceramic tube 17. An external heater 21 is used to initiate and sustain the combustion inside ceramic tube 17.

The flow rate of fuel from fuel supply 18 and the flow rate of oxidant from oxidant supply 16 are controlled to supply an excess of fuel to ensure that the combustion inside ceramic tube 17 occurs under sufficiently reducing conditions to result in the conversion of sulfur-containing compounds to form sulfur monoxide but not significant quantities of hydrogen sulfide. Alternatively, the flow rate of oxidant from oxidant supply 8 may be adjusted to provide sufficient oxidant to the second burner assembly 14 so that oxidant supply 16 is not required.

The gaseous products from the combustion reaction inside ceramic tube 17 are withdrawn from ceramic tube 17, by means of vacuum pump 13 and transferred via a transfer line 22 connected to the second burner assembly outlet tee 20 to a chemiluminescent reaction chamber 23 of the chemiluminescence detector 24.

In the chemiluminescent detector 24 a supply of air or oxygen 25 is connected to an ozone generator 26 and the effluent of the ozone generator 26 is transferred via the ozone inlet line 27 to the chemiluminescent reaction chamber 23 and mixed with the gaseous products from the second burner assembly 14. In chemiluminescent reaction chamber 23, ozone reacts with sulfur monoxide from the second burner assembly 14 to produce sulfur dioxide in an electronically excited state. The electronically excited sulfur dioxide relaxes by emission of light in the blue and ultraviolet region of the spectrum. The emitted radiation is detected by a light detection system 28 which can be a photomultiplier tube, photodiode or array of photodiodes or any similar light detection system. An optical filter 29 can be placed between the chemiluminescent reaction chamber 23 and the light detection system 28 to limit the wavelengths of radiation reaching the light detection system 28. The reaction products in the chemiluminescence reaction chamber 23 are exhausted from the chemiluminescence detector 24 by means of the vacuum pump 13 via the chemiluminescence exhaust line 30. A chemical trap 31 can be installed between the exhaust line 30 and the vacuum pump 13 to remove ozone and other reactive gases from the gas stream prior to entering the vacuum pump 13. The vacuum pump may also be equipped with a gas ballast (not shown) and oil coalescing filter 32 to facilitate venting of water vapor and other gases from the vacuum pump. The vacuum pump is operated so as to maintain the chemiluminescent reaction chamber 23 and the second burner assembly 14 at reduced pressure. For example the chemiluminescent reaction chamber 23 may be operated at <10 torr and the second burner assembly 14 operated at <200 torr.

The signal from the light detection system 28 can be processed by electronic means 33, such as a picoammeter and the electrical signal directed to an electronic integrator and data collection system 34 for further processing.

Figure 2:
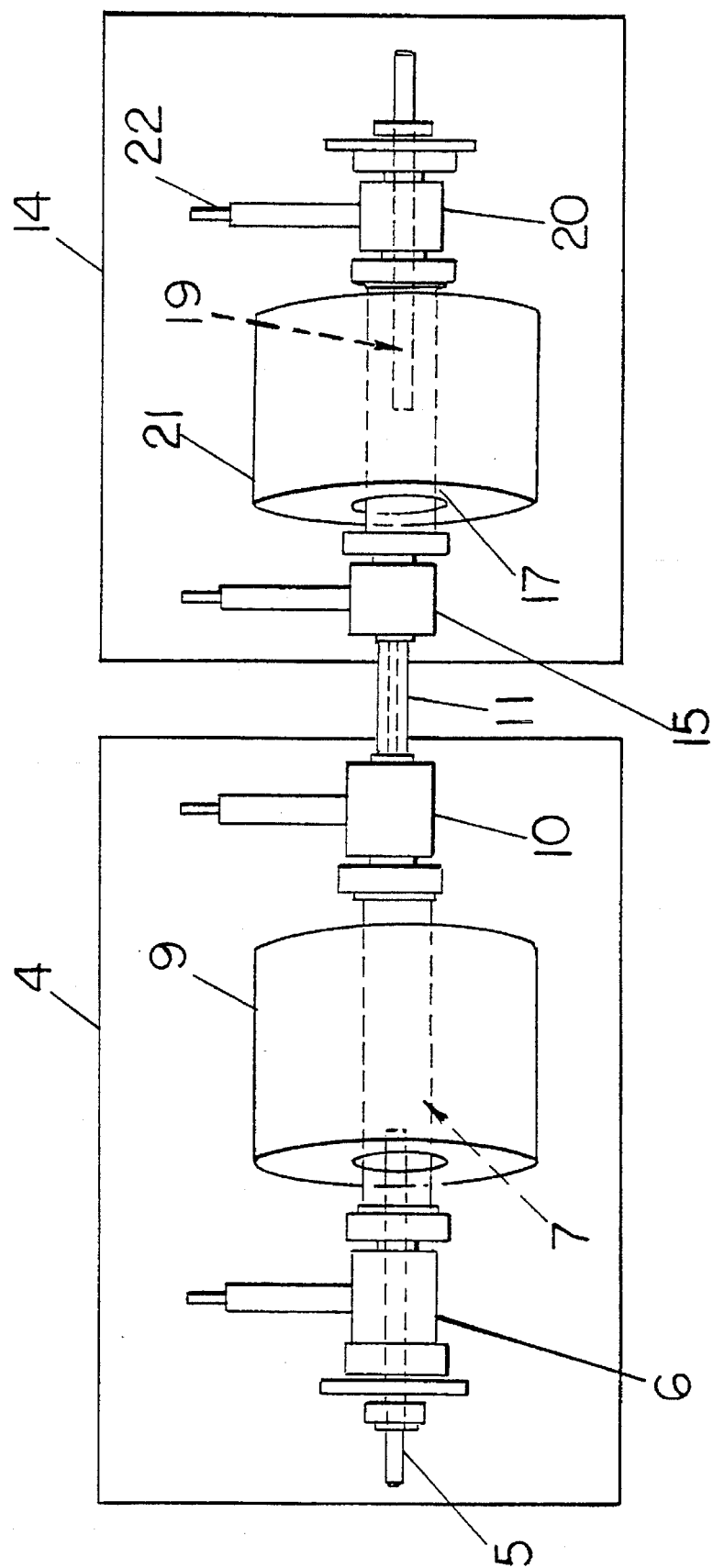
FIG. 2 is a schematic diagram of the burner portion of the invention.

A more detailed schematic of the dual burner assemblies of the present invention is shown in FIG. 2. In one embodiment, the restrictor tube 5 is a ceramic tube having an outside diameter of approximately 0.05" and an inside diameter of approximately 0.02". The restrictor tube 5 extends through the mixing tee 6 and into the combustion tube 7. The combustion tube 7 is a ceramic or quartz tube having an outside diameter of approximately 0.25" and an inside diameter of 0.125". The length of the combustion tube 7 and the flow rates of gases can be optimized to provide sufficient reaction time to ensure complete combustion of the sample. In one embodiment, the combustion tube 7 is a one foot length of quartz tubing, wrapped with Nichrome wire as the external heater 9 and the temperature of the combustion tube 7 was approximately 550° C. The oxidant supply 8 air operated at a flow rate of approximately 150 mL/min.

A portion of the gaseous products from combustion tube 7 are transferred to the second burner assembly 14 by means of the second burner assembly inlet restrictor 11 and a vacuum pump (not shown). In one embodiment, the second burner assembly inlet restrictor 11 was a 3" length of 1/16" outside diameter PEEK tubing having an inside diameter of 0.01". Use of this restrictor permitted collection of approximately 20 mL/min of the combustion gases from the first burner assembly; however, other restrictors can be used to collect more or less of the combustion gases.

In one embodiment of the second burner assembly 14, the ceramic tube 17 is a 4.2" length of alumina tubing having an outside diameter of approximately 1/8" and an inside diameter of approximately 1/16". The fuel delivery tube 19 is a 3" length of alumina tubing having an outside diameter of 0.05" and an inside diameter of 0.02". A commercial heating element (Watlow) was placed around the ceramic tube 17 as the external heater 21 and the temperature was maintained at approximately 800° C. by means of an external temperature controller (not shown).

In one embodiment, the fuel supply 18 was hydrogen gas operated at a flow rate of approximately 100 mL/min and the oxidant supply 16 was not used.

The mixing tee 6, outlet tee 10, second burner inlet tee 15 and second burner assembly outlet tee 20 are standard 1/8" Swagelok stainless steel tees. Transfer line 22 is a 3' length of PFA tubing having a 3/16" outside diameter and a 1/8" inside diameter. Connection for all tubing, tees and transfer lines are made using standard Swagelok nuts and ferrules.

Figure 3:
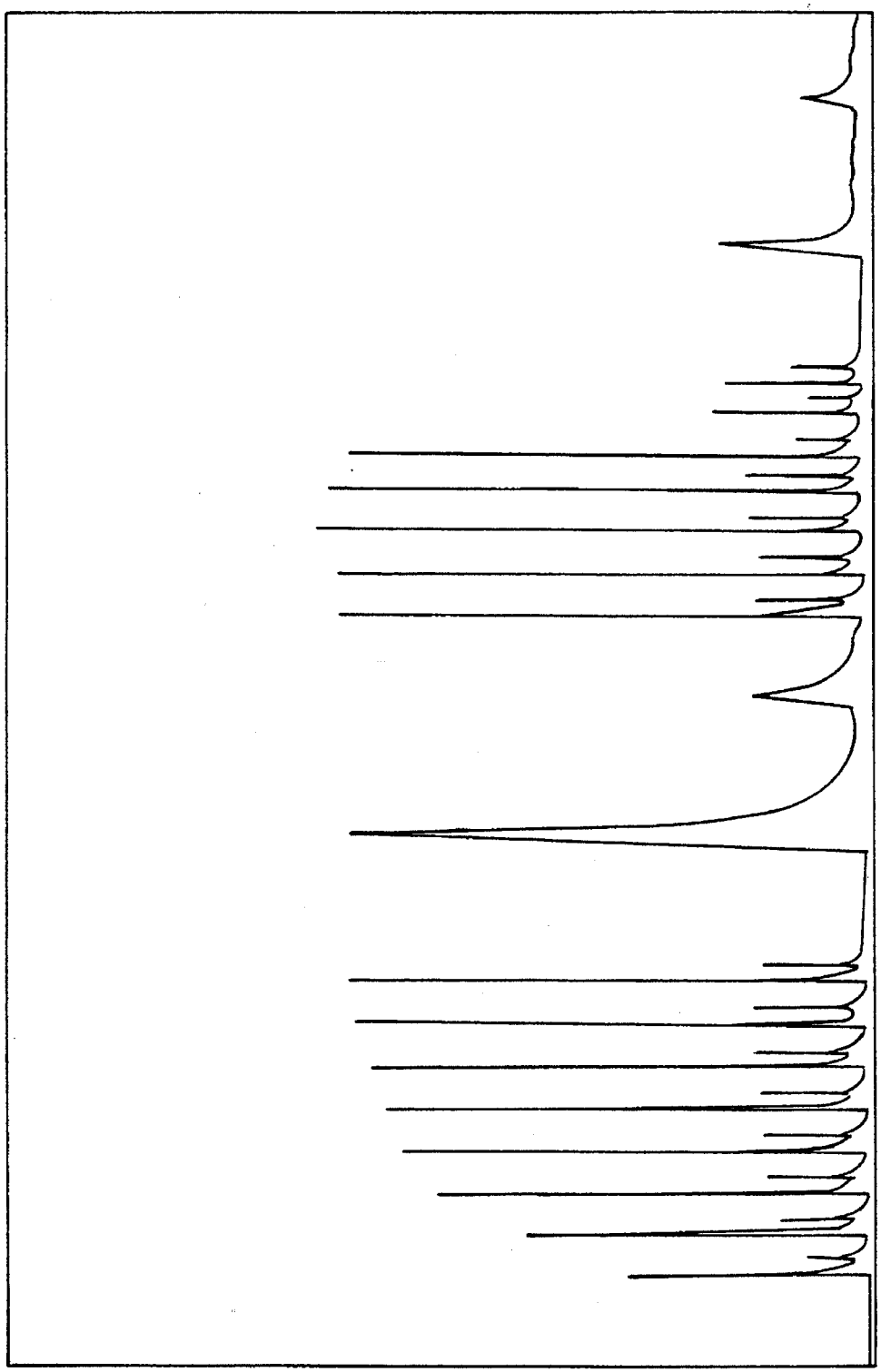
FIG. 3 is a graph showing an example response for a detector in accordance with the invention.

An example of the improved selectivity of the present invention for the measurement of low levels of sulfur compounds in a hydrocarbon matrix is shown in FIG. 3. In this example, the sample inlet system 2 is a ten-port gas sampling valve fitted with two sample loops; 100 microliters and 25 microliters. The sample was propane gas containing approximately 1 part per million of dimethyl sulfide. The carrier gas supply 1 was an air supply operated at approximately 5 mL/min. The gas sampling valve alternates injection of the two sample loops providing injection of different amounts of the sulfur compound into the analyzer. For this example, the chemiluminescence detector 24 is a Sievers Instruments Model 350B Sulfur Chemiluminescence Detector equipped with an Edwards E2M5 vacuum pump. The output of the detector was plotted on a strip chart recorder. FIG. 3 shows the response of the detector for injections of 100 uL and 25 uL of 1 ppm dimethyl sulfide in propane. As shown in FIG. 3 the height of the peaks are significantly greater than the baseline noise.

No detector response is obtained by injection of propane that does not contain sulfur compounds, which illustrates the improved selectivity achieved with the present invention. In contrast, analysis of this same propane sample using the ceramic burner assembly described in U.S. application Ser. No. 07/824,852 by Shearer and the flame-based detector described in U.S. application Ser. No. 07/759,105 by Godec, et al., in conjunction with gas chromatography, produced a large positive hydrocarbon response in addition to the detector response from dimethyl sulfide.

What is claimed is:

1. A device for measuring sulphur in a sample containing sulphur and hydrocarbons, comprising: a first burner means for oxidizing the hydrocarbons in the sample; a second burner means in communication with the first burner means for converting sulphur in the sample to sulphur monoxide; and a chemiluminescence detector in communication with the second burner means for reacting said sulphur monoxide with ozone to produce excited sulphur dioxide and for measuring the chemiluminescence of the excited sulphur dioxide.

2. The device of claim 1, wherein the chemiluminescence detector includes a reaction chamber, an ozone source in communication with the reaction chamber, and a light detector to measure chemiluminescence of the excited sulfur dioxide.

3. The device of claim 2, further comprising a vacuum source in communication with the reaction chamber, to draw the sample through the first burner means, second burner means and reaction chamber.

4. The device of claim 1, wherein the first burner means includes a first burner combustion zone, and means for introducing oxygen into the first burner combustion zone.

5. The device of claim 4, wherein the second burner includes a second burner combustion zone, means for introducing oxygen into the second burner combustion zone, and means for introducing a fuel into the second burner combustion zone.

6. The device of claim 5, wherein the means for introducing oxygen into the first burner combustion zone includes an oxygen supply in communication with the sample for adding oxygen to the sample before it is introduced into the first combustion zone.

7. The device of claim 6, wherein the means for introducing oxygen into the second burner combustion zone is said transfer line, whereby the only oxygen source of the second burner is uncombusted oxygen from the first burner means.

8. The device of claim 6, wherein the means for introducing oxygen into the second burner combustion zone includes an oxygen supply in communication with the second combustion zone for adding oxygen into the second combustion zone.

9. The device of claim 8, wherein the first burner means and the second burner means are in communication via a transfer line which transfers the sample from the first burner means to the second burner.

10. The device of claim 9, wherein the means for introducing oxygen into the second burner combustion zone includes means for introducing oxygen into said transfer line to be transferred to the second burner.

11. A method of detecting sulphur in a sample containing sulphur and hydrocarbon, comprising: oxidizing the hydrocarbons in a first combustion step in a first burner, converting the sulphur to sulphur monoxide in a second combustion step in a second burner, reacting ozone with the carbon monoxide to produce excited sulphur dioxide, and measuring the chemiluminescence of the excited sulphur dioxide to detect sulphur in the sample.

12. The method of claim 11, wherein the first combustion step and second combustion step does not convert a significant portion of sulfur to hydrogen sulfide.

13. The method of claim 11, wherein the first burner and the second burner are in communication by a first transfer line.

14. The method of claim 13, wherein the measuring of chemiluminescence of the excited sulfur dioxide is in a reaction chamber separate from the first burner and second burner and in communication with the second burner by a second transfer line.

15. The method of claim 14, wherein the sample is drawn through the first burner, second burner and reaction chamber by a vacuum source in communication with the reaction chamber.

16. The method of claim 11, wherein said first combustion step occurs in an excess of oxidant.

17. The method of claim 16, wherein said first combustion step includes adding oxygen to the sample.

18. The method of claim 17, wherein said second combustion step includes adding fuel to the sample after the first combustion step.

19. The method of claim 17, wherein said second combustion step includes adding additional oxygen to the sample after the first combustion step.

20. The method of claim 17, wherein said second combustion step does not include adding additional oxygen to the sample after the first combustion step.

* * * * *